United States Patent
Ashby et al.

(10) Patent No.: US 8,898,043 B2
(45) Date of Patent: Nov. 25, 2014

(54) CUSTOMISED SURGICAL APPARATUS

(75) Inventors: Alan Ashby, Leeds (GB); Harald Bornfleth, Fuerstenfeldbruck (DE); Michael Anthony Bowes, Manchester (GB); Ian Michael Scott, Manchester (GB); Graham Richard Vincent, Manchester (GB); Michal Slomczykowski, Buchrain (CH)

(73) Assignees: Depuy International Ltd., Leeds (GB); Depuy Orthopadie GmbH, Feldkirchen (DE); Imorphics Ltd., Manchester (GB)

( * ) Notice: Subject to any disclaimer, the term of this patent is extended or adjusted under 35 U.S.C. 154(b) by 718 days.

(21) Appl. No.: 12/919,769

(22) PCT Filed: Feb. 26, 2009

(86) PCT No.: PCT/GB2009/000517
§ 371 (c)(1),
(2), (4) Date: Dec. 15, 2010

(87) PCT Pub. No.: WO2009/106816
PCT Pub. Date: Sep. 3, 2009

(65) Prior Publication Data
US 2011/0093108 A1    Apr. 21, 2011

(30) Foreign Application Priority Data
Feb. 27, 2008   (GB) .................................. 0803514.9

(51) Int. Cl.
*G06G 7/48*   (2006.01)
*A61B 19/00*   (2006.01)
*A61F 2/30*   (2006.01)
*A61B 17/17*   (2006.01)

(52) U.S. Cl.
CPC ....... *A61B 19/50* (2013.01); *A61F 2002/30948* (2013.01); *A61F 2/30942* (2013.01); *A61B 17/175* (2013.01); *A61B 17/17* (2013.01)
USPC ................ 703/6; 382/131; 382/132; 382/263

(58) Field of Classification Search
CPC ........... G06T 2207/10072; G06T 2207/10081; G06T 2207/10116; G06T 2200/00; G06T 2200/04; G06T 2200/08; G06T 2201/00; G06F 2217/16; A61B 17/17; A61B 17/56; A61B 19/50
USPC .............. 703/2, 6; 378/4, 8, 9, 19, 20, 21, 62; 382/131, 132, 218, 264
See application file for complete search history.

(56) References Cited

U.S. PATENT DOCUMENTS 5,768,134 A   6/1998   Swaelens
5,824,085 A   10/1998  Sahay
(Continued)

FOREIGN PATENT DOCUMENTS

EP          1348394 A1    10/2003
WO          WO 93/25257 A1   12/1993
(Continued)

OTHER PUBLICATIONS
Chinese Patent CN200980106813.6; First Office Action dated Mar. 22, 2012.
(Continued)

Primary Examiner — David Silver
Assistant Examiner — Andre Pierre Louis

(57) ABSTRACT

A method for producing a customized surgical instrument or prosthesis for a specific patient is described. At least one x-ray image of a body part of the patient is captured. A statistical model having a dense set of anatomical correspondence points across the model is instantiated using image data derived from the at least one x-ray image to generate a patient specific model of the body part having a high accuracy surface. Patient specific data from the patient specific model is used to generate a design of the customized surgical instrument or prosthesis for use in a surgical procedure to be carried out on the body part. The surgical instrument or prosthesis is then manufactured using the design. A computer implemented method for generating the patient specific model of the body part is also described.

19 Claims, 4 Drawing Sheets

(56) References Cited

U.S. PATENT DOCUMENTS

| | | |
|---|---|---|
| 6,205,411 B1 | 3/2001 | DiGioia, III |
| 6,711,432 B1 | 3/2004 | Krause |
| 7,194,295 B2 | 3/2007 | Vilsmeier |
| 7,227,981 B1 | 6/2007 | Fleute |
| 7,584,080 B2 * | 9/2009 | Taylor et al. ............... 703/2 |
| 8,112,142 B2 * | 2/2012 | Alexander et al. ............ 600/407 |
| 2005/0015003 A1 | 1/2005 | Lachner |
| 2005/0027492 A1 | 2/2005 | Taylor |
| 2005/0065628 A1 | 3/2005 | Roose |
| 2005/0101966 A1 | 5/2005 | Lavallee |
| 2007/0014452 A1 * | 1/2007 | Suresh et al. ............. 382/128 |
| 2008/0039711 A1 | 2/2008 | Feilkas |
| 2008/0219985 A1 * | 9/2008 | Thompson et al. ........ 424/139.1 |
| 2009/0089034 A1 * | 4/2009 | Penney et al. .............. 703/11 |

FOREIGN PATENT DOCUMENTS

| | | |
|---|---|---|
| WO | WO 0237423 A2 | 5/2002 |
| WO | WO 2004110309 A2 | 12/2004 |
| WO | WO 2007045000 A2 | 4/2007 |

OTHER PUBLICATIONS

GB Search Report GB0803514.9, dated Jun. 30, 2008.

PCT International Search Report and Written Opinion dated Oct. 6, 2009.

Twining, Carole J. et al; "A Unified Information-Theoretic Approach to Groupwise Non-Rigid Registration and Model Building" in proceedings of Information Processing in Medical Imaging, Springer Lecture Notes in Computer Science vol. 3565/2005; 19th International Conference, IPMI 2005, Glenwood Springs, Co, USA, Jul. 10-15, 2005.

* cited by examiner

CUSTOMISED SURGICAL APPARATUS

CROSS REFERENCE TO RELATED PCT APPLICATION

This application is a National Stage 35 U.S.C. 371 of International Patent Application PCT/GB2009/000517 filed Feb. 26, 2009, which claims benefit of priority of United Kingdom Application No. GB 0803514.9, filed Feb. 27, 2008 (now abandoned).

BACKGROUND OF THE INVENTION

The present invention relates to customising surgical apparatus and in particular to customising surgical instruments and/or implants using patient specific data obtained from a captured image of a patient.

The general idea of creating a patient specific instruments or implants from CT or MRI data has been described previously, for example in U.S. Pat. No. 5,768,134 and WO 93/25157. U.S. Pat. No. 5,768,134 describes using a CT scanner or MRI scanner to generate digitized medical information, which can be used with additional digital information, and a rapid prototyping method to create a prosthesis matching a body part and to which a further functional element can be attached. WO 93/25157 describes a method using tomographic data, such as from a CT or MRI scan, and image processing to generate a 3D reconstruction of the body part, which can be used with a CNC machine to allow an individual prostheses to be created. An individual template can also be manufactured matching a patient's anatomy and for mounting on the patient for guidance, alignment and positioning of a treatment tool.

However, not all medical facilities have access to CT or MRI scanners. In many cases, CT or MRI data of a patient is not available. Further, CT scans entail a significant radiation dose for patients and so should be avoided where possible. Further in many countries, regulations require the scans to be diagnosed by a specialist radiologist. Furthermore, CT and MRI scans are data processing intensive and require a large amount of processing time in order to derive patient specific data from the scans. Processing of the data can not be fully automated due to the variability in data quality and the accuracy in surface reconstructions required thus making such an approach unsuitable for a large-scale production scheme.

Other approaches to generating a 3D model of a patient's anatomy exist. For example statistical shape model and other deformable model based approaches can be used for modelling patient's actual bone shapes. For example, U.S. Pat. No. 7,194,295 describes a method for computer assisted navigation and/or pre-operative treatment planning in which a generic model of the patient's body part is adapted based on patient characteristic data which can be obtained from X-ray images of the patient. US2005/0027492 describes a method of building a statistical shape model by establishing correspondences between sets of two dimensional or three dimensional shapes. However, the approaches described in these documents have not in themselves been able to generate 3D models which can efficiently be used to replace CT or MRI scans in the above described methods. Such modelling approaches do not in themselves produce the surface accuracy, for example 1-2 mm, generally required for customising implants or instruments.

Therefore, it would be desirable to be able to provide customised implants, instruments or surgical procedures without using a CT or MRI, or similar, 3D scanning approach.

BRIEF SUMMARY OF THE INVENTION

The present invention does so by providing a modelling approach resulting in a model with a high level of surface accuracy which can be used to produce customised instruments, implants or to customise a surgical procedure to a specific patient's anatomy.

According to a first aspect of the invention there is provided a method for producing a customised surgical instrument or prosthesis for a specific patient, comprising: capturing at least one image of a body part of the patient; instantiating a statistical model having a dense set of anatomical correspondence points across the model using image data derived from the at least one image to generate a patient specific model of the body part having a high accuracy surface; using patient specific data from the patient specific model to generate a design of the customised surgical instrument or prosthesis for use in a surgical procedure to be carried out on the body part; and manufacturing the surgical instrument or prosthesis using the design.

The at least one image can be at least one x-ray image. However, other 2D imaging technologies can be used to capture patient images such as ultrasound.

Preferably at least two images of the body part are captured. More preferably, the two images are captured from different directions and preferably at approximately 90° to each other.

The patient specific model can have a surface shape which varies by less than approximately 2 mm. Preferably, the surface shape which varies by less than approximately 1 mm. The patient specific model can have a surface shape which varies by approximately 1 to 2 mm from the surface shape of the patient's body part.

Preferably, the body part is a joint or a part of a joint of the patient. For example, the joint may be a hip, knee, ankle, shoulder a part of the spine or other joint of the human body.

The patient specific model can include bone and soft tissue. Soft tissues can include muscles, tendons, menisci, ligaments, articular cartilage and other non-bone structures of the human body.

Generating the design can be based on patient specific data relating to both bone and soft tissue. In this way, any interference with, or damage to, soft tissue by the implant or instrument can be reduced.

The design of the customised surgical instrument can include the shape of the surgical instrument by which it can be mounted on the patient's body part. The design can include the outer shape of the surgical instrument by which it can fit into a space around the patient's body part. The design can include the size of the instrument. The design can include the direction of at least a part of the instrument.

Demographic data about the patient can be supplied to the shape model. The shape model can instantiate a model from a sub-population matching the demographic data of the patient.

The method can further comprise processing at least one x-ray image of the body part to generate a processed patient image. Processing can include generating a pseudo x-ray image from a CT image reconstructed from the statistical model. Processing can further comprise processing the pseudo x-ray image in the same way as the at least one x-ray image of the body part to generate a processed pseudo x-image. The processed patient image and processed pseudo x-ray images can be compared as part of instantiation of the patient specific model of the body part.

Processing can include applying a high pass filter to the image. This can help to remove artifacts from the image which do not correspond to sharp bone edges.

Processing can include generating a differential image. A differential image can be generated from the difference between the images.

Processing can include separating the image into a positive features image and a negative features image.

Processing can include applying a broadening function to features of the differential image. The broadening function can help an optimisation process by helping to highlight features in the differential image that are getting closer to fitting.

Processing can include applying a normalising function to the differential image features. The normalising function can reduce differences between the size of the features in the images. This helps to prevent large features dominating an optimisation process.

The statistical model can be generated using a minimum description length approach to generate the dense set of anatomical correspondences.

The model can be a surface model. The correspondences can be confined to the surface.

The model can be a volume model. The correspondences can be explicit across the entire volume of interest.

Instantiating the patient specific model can include using a quasi-Newton optimisation method.

The method can further comprise using a kinematic model. The patient specific data can be used in the kinematic model to predict or determine the likely kinematic behaviour of the body part. The kinematic model can determine kinematic data specifying the likely kinematic behaviour of the patients body part.

Data from the kinematic model can be used in designing the customised surgical instrument or prosthesis.

According to a further aspect of the invention, there is provided a computer implemented method for generating a patient specific model of a body part, comprising: processing an x-ray image of a body part of a patient to generate a differential patient image which has been filtered and normalised; reconstructing a CT scan type image from a statistical model having a high density of anatomical correspondences and generating a pseudo x-ray image corresponding to the x-ray image from the CT scan type image; processing the pseudo x-ray image in the same way as the x-ray image to generate a differential pseudo image; and optimising a cost function based on the residual between the differential patient image and the differential pseudo image using a quasi-Newton optimisation method to generate a patient specific model of the body part.

Further aspects of the invention provide computer program code executable by a data processing device to carry out the computer implemented method aspect of the invention, and a computer readable medium bearing such computer program code.

BRIEF DESCRIPTION OF THE DRAWINGS

An embodiment of the invention will now be described in detail, by way of example only, and with reference to the accompanying drawings, in which.

DETAILED DESCRIPTION OF THE INVENTION

Figure 1:
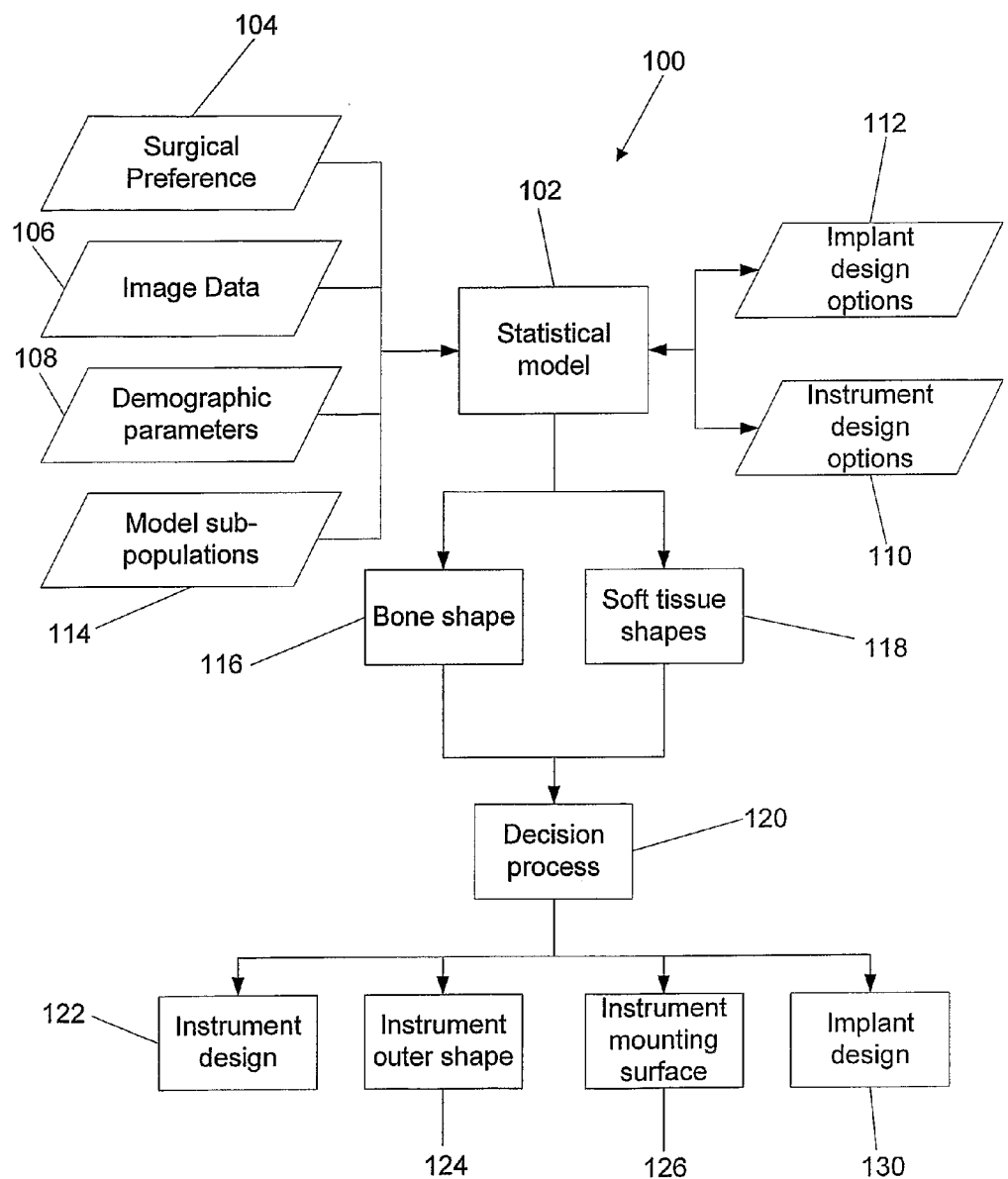
FIG. 1 shows a schematic flow chart illustrating the process of designing a customised instrument.

The present invention uses one or more x-ray images, combined with a statistical model, to provide patient specific anatomy of a joint, or other body part, which can be used to design and manufacture a customised instrument to be used in an orthopaedic procedure on the joint, or to design and manufacture a customised prosthesis for the patient.

In the case of carrying out a surgical procedure of a knee joint, the mechanical axis of the femur and tibia can be calculated from one or more x-ray images of the hip joint and ankle joint, which are referenced into the co-ordinate frame of the x-rays taken of the knee joint and by taking appropriate measurements from the images.

The design of a custom instrument and/or prosthesis can be fully automated by incorporating the features of the bony anatomy and relevant soft tissues relevant for planning into the statistical model.

For example, for a custom knee instrument to be used on the femur, the centre of the femoral head, the epicondyles, the most distal portion of the intramedullary canal, and the most distal points on the condyles can be used to estimate the mechanical axis, femoral rotation, and the joint line. Furthermore, parts of the joint surfaces could be modelled to determine contact surfaces for the instrument. The instrument can be a custom femoral cutting guide to be used during a total knee replacement procedure, that fits at a unique position to the contact surfaces derived from the model and which are reproduced in negative form on the instrument. Similarly, a custom tibial cutting guide can be manufactured from the model, incorporating model knowledge about the tibial mechanical axis, the shape of the tibial plateaus, and contact surfaces that can serve as attachment sites for the tibial instrument.

Custom instruments can also be applied to hip surgery, e.g. for a hip resurfacing procedure. Here, for example, the statistical model provides information about the direction of the femoral neck axis so that a custom drill guide can be manufactured for positioning the resurfacing implant. The surfaces of the femoral head generated by the mode are used to determine contact surfaces for the drill guide, which are reproduced in negative form on the instrument to allow a unique positioning of the drill guide on the femoral head.

An example of a custom implant could be a custom-made unicondylar knee implant that reproduces the patient's condylar shape on only one of the condyles, with the other condyle staying in place during surgery. Another example is a femoral implant with different, patient-specific, radii of the medial and lateral condyles.

The statistical shape model can include sub-populations, each exhibiting a certain property. For example, the statistical shape model can include patients with valgus knee geometry. That a particular patient belongs to a sub-population of patients can be identified when instantiating the model either automatically from the x-ray data being used to instantiate the model or can be indicated manually by tagging or other wise identifying the data as belonging to a specific sub-population. Depending on the sub-population that the patient falls into, the design of the custom instrument and/or prosthesis can vary. For example, if the patient has a valgus knee deformity, there may be different surfaces available for matching the instrument, e.g. a cutting block, to the bone shape, compared to a varus knee or a knee with a normal geometry. Similarly, different classes or types of prosthesis may be more appropriate for knees exhibiting different types of deformity. This allows an automated selection between different design options for instruments and/or prostheses. One design option can be less sensitive to a possible mal-orientation by the surgeon than another one for a given surface geometry. Hence, in this way, the robustness of the design solution used in the surgical procedure can be improved.

The geometry of the custom instrument or prosthesis can vary. This variability can also be encoded into the statistical model of the bone, so that the shape of the instrument can be optimised according to the geometry of the bone. This is not limited to the matching surface of the instrument by which it can be mounted on the bone, but also includes the outer surfaces of the instrument which can be varied to take into account the space into which the instrument needs to fit.

Soft tissue structures can also be included into the statistical shape model, e.g. the patellar tendon. The shape of the instrument can be adapted so as to minimize interference with the soft tissue structures during the surgical procedure.

With reference to FIG. 1 there is shown a schematic flow chart type diagram 100 illustrating the various data sources, inputs and outputs used by a statistical model 102 and as part of the customised instrument and/or prosthesis design process. At the heart of the process is a particular type of statistical model 102 which can generate a 3D model of a patients anatomy which has highly accurate surfaces. That is the surface of the customised model of the patient's bone should correspond to the actual surface of the patient's bone within a variation of about 1 to 2 mm and preferably within about 1 mm. The statistical model used and how the statistical model is instantiated using x-ray images of the patient's anatomy are described in greater detail below.

Surgical preference data 104 can be provided to the statistical model. The surgical preference data 104 indicates at least which joint or body part the surgical procedure is going to be carried out on so that the shape model can instantiate a model of the appropriate body parts for the surgical procedure, e.g. a tibia and femur for a knee replacement procedure. The surgical data can include other date indicating, for example, the surgical approach being used, as different surgical approaches can be taken to the same general procedure, e.g. a knee replacement procedure. The surgical approach data can also indicate whether a minimally invasive surgical approach is being used. The surgical data 104 can also indicate whether any soft tissue strategy is going to be used and if so what strategy.

Bone surface information from 3D models built from CT images, which show only the bone, is combined with 3D models built from other imaging modalities which can display soft tissue, such as MRI images, or ultrasound images. This can be achieved, for example, by building a single model from sets of registered MR and CT data from the same patient or using a separate MR soft tissue model which is registered to the bone surface by virtue of the similarity of the bone shape or other features. In either case, given only the bone surface for a particular individual estimated from radiographs, the statistical model provides an estimate of the most likely soft tissue structure for the particular individual.

Hence, soft tissue structures important to surgery, such as the articular cartilage and the ligaments and tendons of the joint, can be estimated. For example, an estimate of the thickness of articular cartilage provides a more accurate description of the 3D-surface to which the instruments will be attached, leading to greater precision in the surgery. Similarly, an estimate of the size and position of the patellar tendon will allow the surgery to be planned, and the instrument constructed, so as to preserve this important structure.

Further, the statistical model can predict and advise on the extent of correction needed to achieve a knee geometry that is the most probable estimate of a healthy knee for the particular patient. Data specifying the patient specific anatomy from the statistical model can be passed to a software kinematic model which can apply the patient specific anatomical data to determine the kinematic behaviour of the patient's joint, for example a knee joint. Data relating to the patient specific kinematic behaviour of the joint can then be provided to the design process so that instrument and/or implant design can also be based on the kinematic behaviour rather than just static behaviour. For example, the position of a cutting block or cutting guide defined by a cutting block could be adjusted so as to specifically compensate for or correct a kinematic behaviour of the knee. Similarly, the shape or configuration of an implant can be adjusted based on the data specifying the patient specific kinematic behaviour of the joint to take into account a predicted patient specific kinematic behaviour of the joint.

In addition, data specifying the kinematic behaviour of a knee joint, and which is correlated with different deformations of the knee, can be identified automatically by the software, and can be used during the modelling phase to inform the user of potential soft tissue releases that can be carried out during the surgical procedure, such as which ligaments to be released and the extent of release. For example, the data can specify: bone osteophytes located in the posterior part of the posterior condyles, which are associated with limited knee flexion; specific knee alignment deformations (e.g. varus or valgus deviation of the mechanical axis of the femur and tibia), which is associated with varus or valgus flexion deviation of the knee joint; missing (damaged or underdeveloped) femoral condyles associated with abnormal (flexion or flexion and rotation) knee kinematic behaviour (rotational instability).

Image data 106 includes data derived from X-rays or other projection images captured of the patient's anatomy. The X-ray date is obtained from x-ray images that have been processed to improve the accuracy of the surfaces of the instantiated model as is described in greater detail below. The image data can also be processed to provide further input to the statistical model to help generate a more accurate model. For example, in the case of a knee joint, the image data can be processed to help identify the state of the knee. If the angle between the femoral and tibial axes is substantially less than 180° then the knee can be classified as having a varus deformity, if the angle is substantially greater than 180° then the knee can be classified as having a valgus deformity, and if the angle is close to 180° then the knee can be classified as having a normal geometry. This information can then be used by the statistical model to instantiate a model based on data from a population having the corresponding class of knee.

Demographic parameters 108 relating to the patient can also be supplied to the statistical model. For example, demographic parameters can include information such as the age, gender, ethnicity, body mass index, height and other details relating to the patient. The demographic parameter data can be used by the statistical model to select data for a corresponding sub-population, e.g. old females, for use in instantiating the model, so as to improve the accuracy of the model of the patient's body parts.

Data defining model sub-populations 114 can also be provided as input and encompasses models that are specific to patient data known pre-operatively for different sub-populations of people defined a particular condition, e.g. a subpopulation of people having varus or valgus deformity.

Other information that can be supplied to the model, includes data specifying the previous medical history of the patient. For example, a meniscus removal may have an impact on a surgical plan automatically generated from the model.

Instrument design option data 110 is also provided. The instrument design option data specifies the different ways in which an instrument design can be varied so as to be customised for the specific anatomy of the patient. For example, different versions of a type of instrument for varus knees, valgus knees, and normal knees could be selected by the model. As another example, in a knee procedure, the joint space may be modelled, and the distal part of the femoral cutting guide adjusted so as to fit into the joint space.

For example, the instrument design option data can specify which parts of the instrument are going to provide the matching surface or surfaces by which the instrument can be mounted on the patient's body for. In the case of a customised femoral cutting guide instrument, the cutting guide is provided with a number of surface areas, preferably at least three, but at least enough surfaces or surface area, that matches the shape of the surface of the femur of the patient, so that the cutting guide can be mounted on the femur in a single position, which is uniquely defined by the matching surface or surfaces of the instrument. By customising the instrument in this way, it is not necessary to navigate placement of the instrument as it can only be attached to the patient's femur in a single way and so is automatically navigated to the correct location on the femur. The cutting guides in the instrument have a known relationship to the matching surfaces and so it is possible to mount the cutting guides at a pre-selected position relative to the femur to allow the femoral cuts to be made.

The instrument design option data 110 can also include soft tissue interference information indicating how any soft tissue structures might interfere with a particular design of instrument and so allowing the instrument design to be customised to try and avoid or reduce any soft tissue interference. For example, a tibial cutting guide can be designed so as to match to the medial frontal surface of the tibia. The matching surface will be bordered by the patellar tendon. Interference with the tendon would reduce the accuracy of placing the instrument on the surface, or, alternatively, the tendon might need to be damaged to carry out the procedure. This can be prevented by incorporating information about tendon attachment sites into the model.

Dependent on the model of the patient's bone and the type and extent of surgery, custom instruments can be designed individually to preserve cruciate ligaments (anterior, posterior or both) and/or to preserve menisci.

For implant design the model can obtain data 112 specifying different implant design options and the decision on implant shape is made based on the geometry of the statistically modelled shape of the femur and tibia and statistically modelled shape of the soft tissues (ligaments and menisci and cartilage) and its implications on kinematics. Specifically, the anterior-posterior (AP), medial-lateral (ML) size of the implant, curvatures of implant condyles and shape allowances for preserving the anterior and posterior cruciate ligaments (ACL, PCL) are determined based on the information provided by the statistical model. In addition, the model can be used to design a custom patella and to customize the patella-femoral interface. Some discrete dimensions of the femoral and tibial condyles (such as AP or ML dimensions or condyles radii), origin and insertion of the ACL, PCL and collateral ligaments, insertion and origin of patellar tendon, and menisci locations can be used to define the final, customised shape of the implant. As a further example, the statistical model could find that in a knee joint, only one condyle was damaged, and therefore select a uni-condylar knee implant instead of a total knee implant.

Based on the various input data sources described above, the statistical model is instantiated using the patient x-ray derived data, as described below with reference to FIG. 2, and can output data specifying the bone shape or shapes for the patient and/or the surface soft tissue shape or shapes for the patient. For example, the model may output data specifying the shape of the surface of the proximal part of the patient's tibia, the shape of the surface of the distal part of the patient's femur and the attachment site geometry of the patellar tendon, the rectus femoris tendon and the medial and lateral collateral ligaments for a knee replacement procedure.

A decision process 120 then uses the patient specific bone shape data and/or soft tissue shape data in order to design a customised instrument and/or prosthesis. For example, if the instrument to be designed is a femoral cutting block, then a generic model of a femoral cutting block instrument may be scaled to more accurately match the size of the instantiated model of the patient's femur. Various data items 122 specifying the overall design of the instrument are generated and output by the decision process. The decision process 120 can also compute the outer shape of the instrument 124 by taking into account the space in which the instrument must fit and to reduce or avoid interference with soft tissue structures, based on the soft tissue shape information 118. The decision process 126, also computes the shapes that the matching parts of the instrument need to have in order to allow the instrument to be mounted at a unique position on the patient's bone, using the bone shape data 116.

The surfaces modelled for providing the unique attachment sites of the instrument can be specific surfaces close to the joint, where little osteophytes or other strong deviations from the bone shape reconstructed by the statistical model occur. These surfaces can be modelled with high accuracy and can be used as mating surfaces for the patient specific instruments.

If a customised prosthesis is additionally, or alternatively, to be designed for the patient, then the decision process can also generate a customised implant design 130 by selecting a generic implant design for the body part, e.g. a femoral knee implant, and then customising the design of the implant based on the patient's bone shape data 116 to more closely match the shape of the patient's actual anatomy or in some other way to make the implant more suitable for the surgical procedure, e.g. to help correct a valgus deformity.

The statistical model generates the patient specific bone shape. The computer may also inform the user what is the most probable geometry of the entire healthy, pre-morbid knee joint for this patient. This information may serve as a template and goal for reconstructive surgery. The most probable, healthy, pre-morbid shape of the knee joint will be a function of several factors including age, sex, ethnic origin, life style etc and including geometrical models of the healthy knee joint.

Once the instrument and/or implant designs have been completed, then the instrument and/or implants can be manufactured using any suitable manufacturing technique, such as a rapid prototyping or rapid manufacturing technique.

As well as providing image data used for determining the shape of the bone, the image data 106 can provide other anatomical information which can be used in producing the customised instruments and implants. For example, the image data 106 can include data indicating the mechanical axes of the patient's body parts so that this information can be used in designing the instrument and/or implant.

The mechanical axis of a patient's limb can be reconstructed from captured images in a number of ways. For example, for a patient's leg, in a first way, one or more long standing x-rays of the patients leg can be captured. In another way, a set of overlapping x-ray images of the hip, knee and ankle joints can be captured and the images 'stitched' together. In a third way, a set of disjointed images can be captured with a common reference object visible in the images so that the images can be registered together subsequently.

Figure 3:
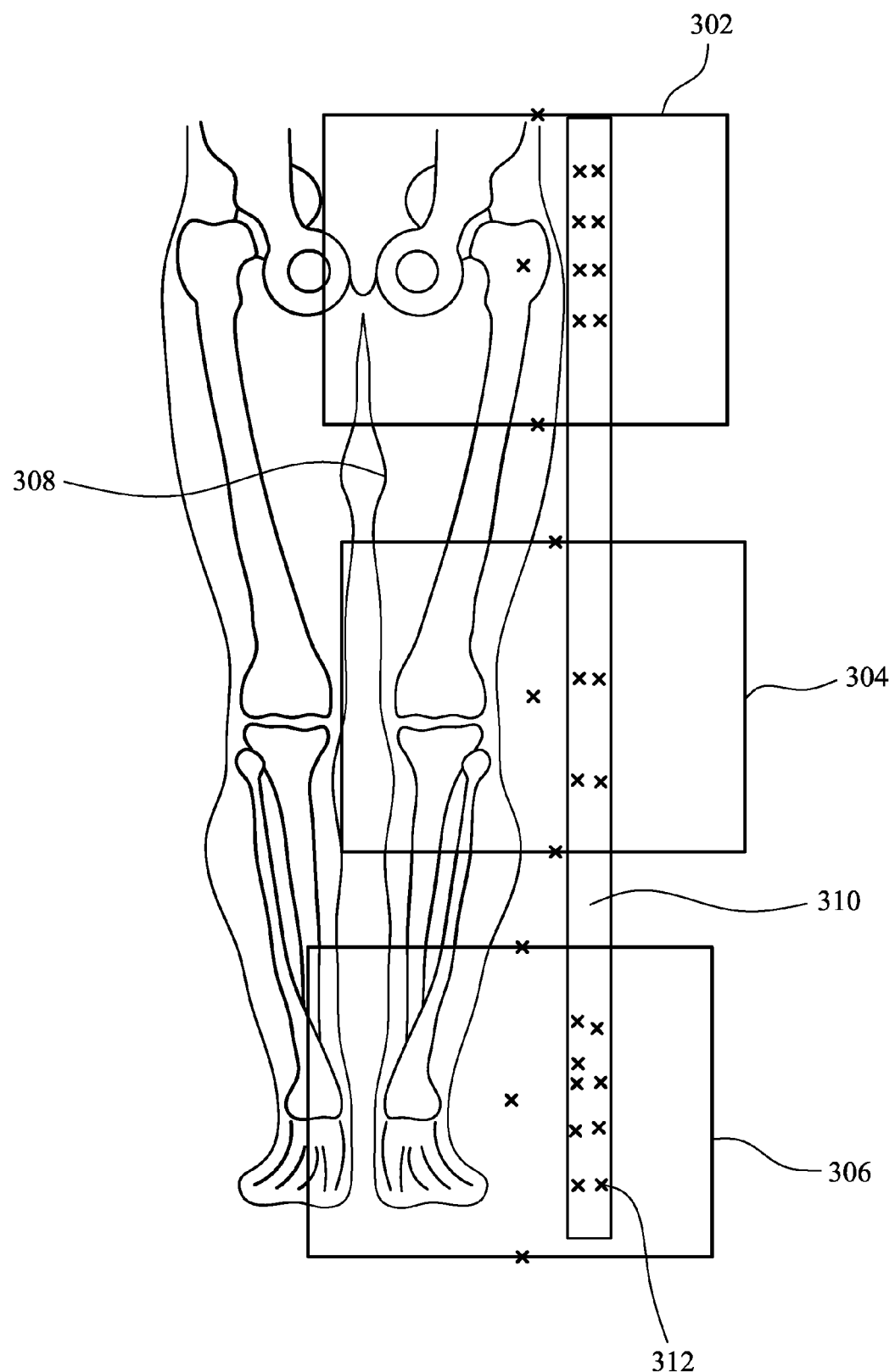
FIG. 3 shows a graphical illustration of imaging different parts of a patient's body.

FIG. 3 illustrates the third way and shows a graphical representation of capturing x-ray images of the hip 302, knee 304 and ankle 306 of a patient's leg 308 and a common reference object 310. The common reference object 310 includes a plurality of x-ray opaque markers 312, or fiducials, which are visible in the resulting x-ray images. As the positions of the markers 312 on the reference object are known, the relative positions of the three x-ray images 302, 304, 306 can be determined from the positions of the markers in the respective images. More than one x-ray can be acquired of each region, e.g. from two different angles to provide three dimensional information. If different angles are used, then additional calibration objects which facilitate referencing of x-rays taken from different angles into a single common co-ordinate frame can be placed in the field of view.

The statistical model can reconstruct a precise bone model of the knee joint surfaces, and can automatically extract anatomical landmarks for planning the surgical procedure, such as epicondyles, the femoral, tibial and mechanical axes, joint line, depth of the tibial plateaus, etc. This provides an automated method for planning surgical cuts as planning software can use the anatomical information specific to the patient to decide where the various cuts should be made for correct positioning of the implants. The custom instrument can then be designed by the decision process to match the specific surfaces of the patient's knee joint, and with cutting guides at the appropriate positions to make the planned cuts, and then the custom instrument manufactured using a rapid manufacturing technique, e.g. stereolithography.

Having described the overall method of the invention, the creation and instantiation of the statistical model used in the method will now be described in greater detail with reference to FIG. 2.

As discussed above previously it has not been possible to use a statistical model approach to generating customised instruments and implants as sufficient accuracy and reproducibility has not previously been available. The present invention uses a number of techniques which it has been found surprisingly allows a statistical model approach to be used, thereby obviating the problems associated with CT and MRI scan based approaches.

The statistical model includes a dense, high-quality set of anatomical correspondences across the model to help provide the surface accuracy required.

Also, pre-processing of the x-ray images is used to help ensure consistent results. A variety of processing techniques can be used as described below.

In order to fit the model in a practicable amount of time a specific optimisation process is used, taking advantage of certain properties of the problem, in order to generate an accurate answer within minutes rather than hours.

Figure 2:
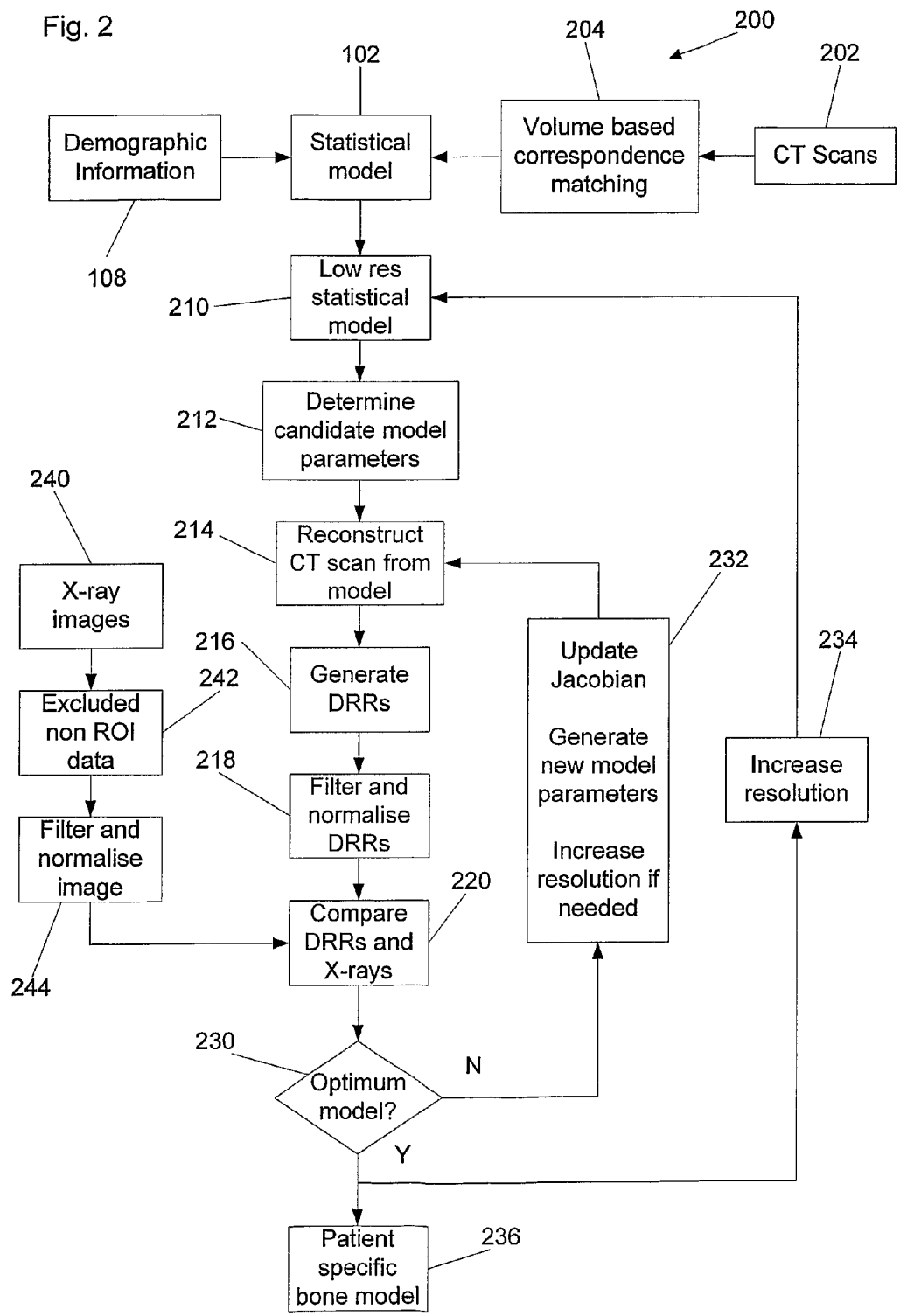
FIG. 2 shows a schematic flow chart illustrating the building and use of a statistical shape model.

FIG. 2 shows a schematic process flow chart 200, illustrating a method for generating a patient specific bone model. The method illustrated by the flow chart can be implemented in practice by suitable software. As illustrated, the statistical model 102 is initially built from CT scans 202 of a large number of different bodies forming the population and various sub-populations on which the statistical model 102 is constructed. The CT scan data is processed using a volume based correspondence matching process 204 in order to create the statistical model having a dense, high quality set of anatomical correspondences. As discussed above, demographic information 108 can be provided to the statistical model when a particular model is being instantiated so that the model uses data for a sub-population which is appropriate for the particular patient.

The statistical model 102 includes a set of correspondence points which can be considered anatomical landmarks for the particular body part being modelled. That is a set of correspondence points exist which mean something anatomically, so that, for example, if the body part is a distal femur and one of the correspondence points is the medial epicondyle, then when an instantiation is created, then the instantiation will have a point which corresponds to the medial epicondyle. This prevents instantiations which while they may be a good fit mathematically are not realistic, e.g. by having the lateral condyle of the instantiation fall on the medial condyle of the model. More specifically, the present statistical model is an appearance model which includes both shape data and image intensity data (also referred to in the art as "texture") which correlates with the shape data.

The key problem is to identify the correspondences in a 3D model. This can be achieved by hand in 2D but is not practical in 3D. Process 204 automatically finds the correspondences in 3D which are then used to build the appearance model 102. A minimum description length approach is used similar to that described in US 2005/0027492 and "A Unified Information-Theoretic Approach to Groupwise Non-Rigid Registration and Model Building" in proceedings of Information Processing in Medical Imaging, Springer Lecture Notes in Computer Science Volume 3565/2005, Carole J. Twining, Tim Cootes, Stephen Marsland, Vladimir Petrovic, Roy Schestowitz, and Chris J. Taylor, the disclosures of which are incorporated herein by reference for all purposes. The model produced can either be a surface model for which the explicit correspondences are confined to a surface, with the CT volume reconstructed using profiles running perpendicular to each correspondence point, or can be a volume model for which there are explicit correspondences across the entire volume of interest.

The optimisation process used in the method to arrive at the optimum model for a given patient using one or more x-rays uses a cost function which is the sum of the squares of the residuals (i.e. the differences between the images of the DRR generated by the model and the x-ray image data) and which is minimised with respect to the parameters of the model. The parameters of the model include 3 angles, 3 positions (the "pose" or position of the model in the CT volume) and a scale parameter and any number of other parameters which can be used in the model.

At step 210 the process begins with a low resolution model and at step 212 an initial set of candidate parameters for the model are selected. The pose parameters are set to an initial set of values, which can be selected manually, and the other parameters of the model can be set to a mean or average value. Then at step 214, using the initial set of parameter values, a 3D volume CT type image is constructed from the model. It is important to try and generate an accurate 3D CT image from the model data and without introducing quantisation effects which can make the cost function too noisy to solve.

Figure 4:
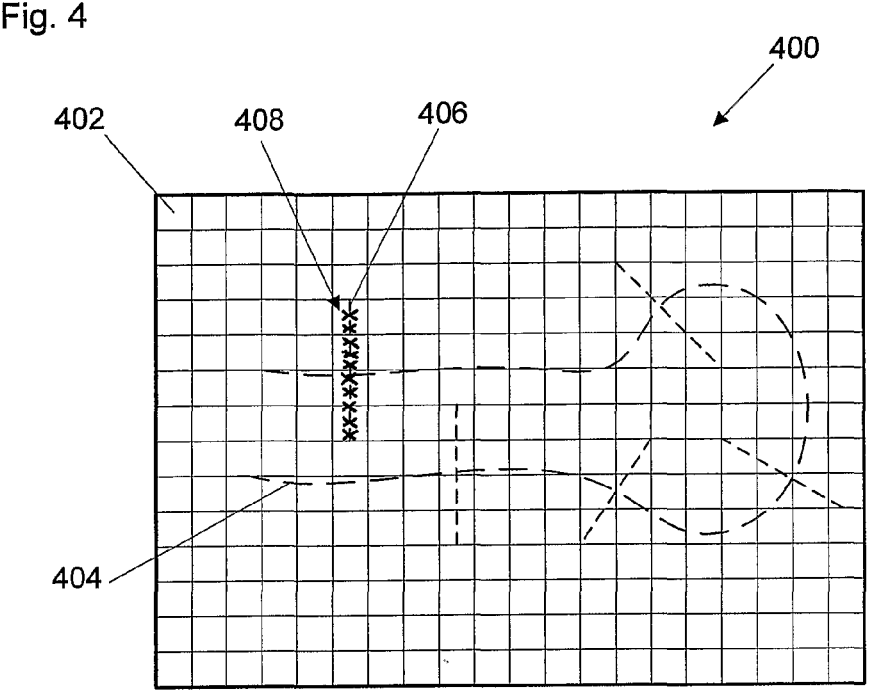
FIG. 4 shows a graphical representation illustrating reconstructing the texture for a CT scan type image.

FIG. 4 shows a schematic representation of a slice 400 of the reconstructed CT image comprising a plurality of voxels, e.g. voxel 402. For a profile modelling approach, the statistical model data provides data specifying the shape of the bone which guides the addition of intensity or texture data in order to reconstruct the CT scan.

For each of a set of points on the shape of the bone 404 of the bone (only five points are illustrated in FIG. 4 for simplicity but in practice a larger number of points is used so as to more accurately reconstruct the texture of the bone), a line, e.g. 406, normal to the local surface of the bone is determined. Then, a value for the intensity is calculated at each of a plurality of points 408 along that line, both inside and outside the bone. The value of the intensity for each point 408 along the normal line 406 is calculated using a reverse linear interpolation process. Multiple sample points 408 may fall in the same voxel, but the value for each sample point calculated as a weighted sum of the intensity of that voxel, based on how far the sample point is from the voxel. The CT volume is reconstructed using a multi-resolution method. In an alternate embodiment, a volume model can be used instead of a profile model. At step 214 the bone profile and texture are determined for all of the slices of the CT image until a CT image has been reconstructed for the current parameters.

Figure 5:
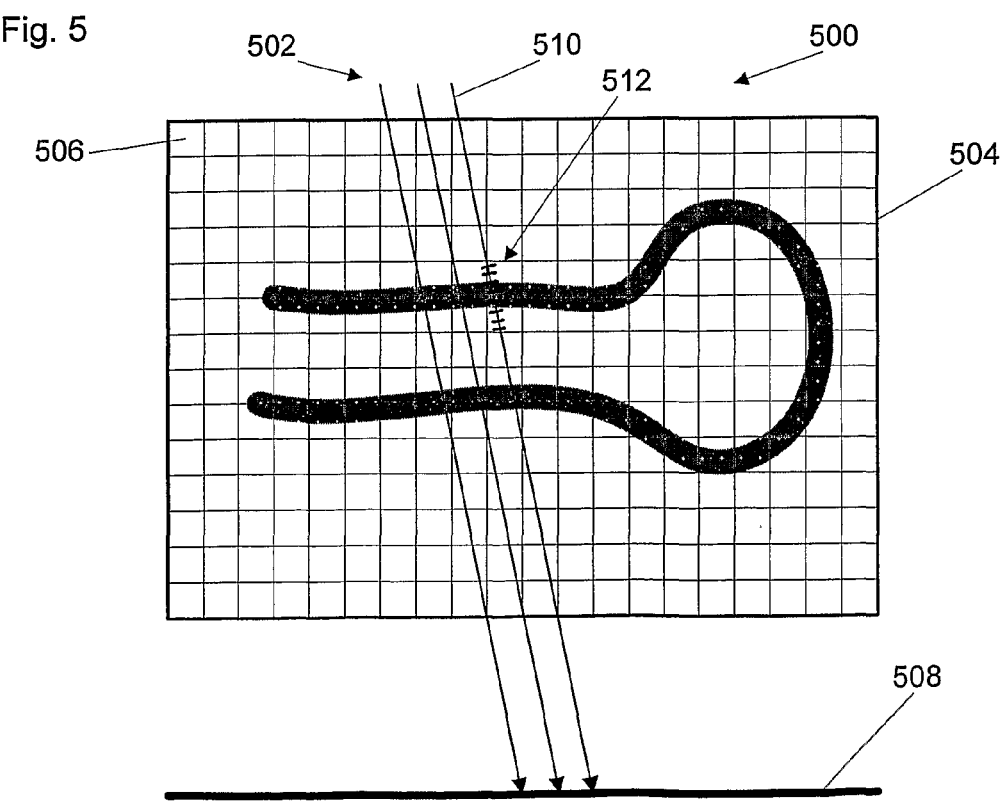
FIG. 5 shows a graphical representation illustrating generating a pseudo radiograph from a CT scan type image

Then at step 216 digitally reconstructed radiographs (DRRs) are generated from the reconstructed CT scan for comparison with the actual projection x-ray images of the patient. FIG. 5 shows a schematic representation 500 of a number of rays 502, passing through the CT image 504 comprising a plurality of voxels 506, and the plane of the projection radiograph 508 that is being generated. As illustrated, each ray, e.g. 510, passes through a plurality of voxels, and a linear interpolation method is again used to calculate the total intensity value for each ray path for the resulting DRR image by sampling values at a plurality of positions 512 along the ray line 510. Each ray line is broken up into sub voxel lengths and a linear interpolation of the CT voxel intensity values is determined for each sampling point so as to calculate the corresponding intensity value for the DRR.

The initial x-ray image data of the patient 240 is subjected to various filtering and normalisation processes in order to prepare the patient image data for comparison with the DRRs generated from the reconstructed CT scan at step 220 of the optimisation process. As an initial step, the data may be filtered to exclude data associated with non regions of interest 242. As illustrated by step 218 the same filtering and normalisation processes are applied to the DRRs, but the normalisation and filtering processes will only be described with reference to the patient image data below. The pre-processing of the patient images helps to remove differences between x-ray images that can result from the imaging process carried out by the hospitals (such different radiography settings, radiographs, radiography procedures or scanning of radiographs).

Rather than working on absolute image intensity values the images are processed to identify edges by working with differences in intensity or brightness. In order to remove non-sharp edges from the image, which are unlikely to correspond to bone edges, a high pass filter is applied to the initial x-ray image data in order to remove edges spanning four or five pixels or more. Also a smoothing filter with a kernel extending over a couple of pixels is applied to the original x-ray image data help remove speckle noise from the image data.

The optimisation process looks at the difference between the differential image of the patient and the differential image of the DRR generated from the reconstructed CT image. It is the square of those differences, or residuals, which is the cost function which is minimised by the optimisation process. An exponential smoothing operator is applied to the differential image data so as to broaden the peaks in the differential image.

As well as applying a smoothing operator to broaden the peaks in the differential image, the differential image is decomposed into positive and negative parts. That is, a half wave rectification type filter is applied so that each differential image is separated into its positive sense peaks and its negative sense peaks. Therefore the image element for each differential image comprises left-right and up-down information for positive peaks, and left-right and up-down information for negative peaks.

As well as filtering the image data, a normalisation procedure is applied to the differential image data at steps 244 and 218. Normalisation can be applied simply to the magnitude of the edge, i.e. simply adjusting the height of the peak, or can be applied to a vector defined by any number of components in the difference image. A tanh, sigmoid or ERF function can be used as the normaliser function to apply to the differential peak heights.

After the image data for patient x-rays from two different directions, and two corresponding DRR images, have been high pass filtered, half-wave rectified, broadened and normalised, the patient and DRR differential image data are subtracted which results in residual images at step 220. The problem then reduces to how to vary the model parameters in order to minimise the residual images. The optimisation approach used is a quasi-Newton optimisation method which is not strictly a quadratic method but is better than a linear method. At step 230, the current model, based on the initial model parameters will not be the best fit and so finite difference are used to find the Jacobian expressing the actual gradient of the cost function (the sum of the squares of the residual values) for the current values of the model parameters. Newton's method is then used to jump to an approximation of the solution and the parameter values are updated to a new estimate which corresponds to the approximate solution.

The residuals for the new parameter values are calculated and the Jacobian updated to correspond to an updated gradient and another Newton jump is made to the next approximate solution. The optimisation method and steps 232 of updating the Jacobian and generating new model parameters are iterated a number of times, as indicated by the process loop in FIG. 2. The resolution used in the reconstruction of the CT scan from the model can be increased if needed 234 to help identify a better solution. The optimisation process can iterate until it is determined at step 230 that a best solution has been found. This may involve carrying out a full finite differences re-calculation of the gradient in a final step as the Jacobian updates tend to accumulate errors. The method can then be repeated using a higher resolution statistical model, but using the model parameters determined from the optimisation process as the initial candidate model parameters at step 212. The optimisation using this method results in a sufficiently accurate answer in minutes rather than the hours required for a conventional non-linear optimiser.

Finally, after as many increases in resolution of the statistical model have been applied as needed for the required surface accuracy, the patient specific bone and/or soft tissue model of the patient is output at step 236. Although the above discussion has focussed on bone structures in x-ray images, it will be appreciated that the general teaching can be extended to cover soft tissue structures in images also. The patient specific bone and soft tissue information is then used in the customised design and manufacture of instruments and/or prostheses as described above with reference to FIG. 1.

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Although the above has generally described the present invention according to specific processes and apparatus, the present invention has a much broader range of applicability. In particular, aspects of the present invention is not limited to any particular kind of surgical instrument, implant or surgical procedure and can be applied to virtually any implant, instrument or procedure where customisation of an instrument or implant would be beneficial. One of ordinary skill in the art would recognize other variants, modifications and alternatives in light of the foregoing discussion.

The invention claimed is:

1. A method for designing a customised surgical instrument or prosthesis for a body part of a specific patient, the body part having a body part surface, the method comprising the step of:
  processing at least one x-ray image of the body part to generate a processed patient image, wherein processing the at least one x-ray image includes filtering the at least one x-ray image, creating a differential image corresponding to differences in intensity of the filtered at least one x-ray image and normalizing peaks in the differential image by applying a normalizer function to the differential image;
  instantiating a statistical model generated using a minimum description length approach and having a set of anatomical correspondence points across the statistical shape model using image data derived from the processed patient image to generate a patient specific model of the body part having a modeled surface, the instantiating step comprising:
  (i) generating a pseudo x-ray image of the body part from a CT image reconstructed from the statistical model using parameters of a model of the body;
  (ii) processing the pseudo x-ray image of the body part to generate a processed pseudo x-ray image, wherein processing the pseudo x-ray image includes filtering the pseudo x-ray image, creating a differential image corresponding to differences in intensity of the filtered pseudo x-ray image, and normalizing peaks in the differential image by applying a sigmoid function to the differential image;
  (iii) comparing the processed patient image and processed pseudo x-ray images to determine the differences between the processed patient image and the processed pseudo x-ray image; and
  (iv) repeating steps (i) to (iii) using different parameters of the model of the body part to minimize a cost function indicating the differences between the processed patient image and the processed pseudo x-ray image and generate the patient specific model; and
  generating a customised surgical instrument or prosthesis having a contact derived from the modeled surface of the patient specific model.

2. The method of claim 1, wherein the patient specific model has a surface shape that varies by less than approximately 1 to 2 mm from the surface shape of the body part.

3. The method of claim 1, wherein the patient specific model includes bone and soft tissue.

4. The method of claim 3, wherein the step of generating the customised surgical instrument or prosthesis is based on patient specific data relating to both bone and soft tissue.

5. The method of claim 1, wherein the contact surface is a portion of the surgical instrument that is shaped to fit on the body part and/or is a portion of the surgical instrument that is shaped to fit into a space around the body part.

6. The method of claim 1, wherein demographic data about the patient is supplied to the statistical shape model and wherein the statistical shape model instantiates a model from a sub-population matching the demographic data of the patient.

7. The method of claim 1, wherein the processing step includes applying a high pass filter to the pseudo x-ray image.

8. The method of claim 1, wherein the processing step includes generating a differential image.

9. The method of claim 8, wherein the processing step includes separating the pseudo x-ray image into a positive features image and a negative features image.

10. The method of claim 8, wherein the processing step includes applying a broadening function to features of the differential image.

11. The method of claim 8, wherein the processing step includes applying a normalising function to the differential image features.

12. The method of claim 1, wherein the statistical shape model is a surface model and the correspondence are confined to the surface.

13. The method of claim 1, wherein the statistical shape model is a volume model and the correspondences are explicit across the entire volume of interest.

14. The method of claim 1, wherein instantiating the patient specific model includes using a quasi-Newton optimisation method.

15. The method of claim 1 further comprising the step of using patient specific data from the patient specific model in a kinematic model.

16. The method of claim 15, wherein the kinematic data is also used to generate the design of the customised surgical instrument or prosthesis.

17. The method of claim 1, wherein the generating step comprises the step of manufacturing the surgical instrument or prosthesis.

18. The method of claim 1, wherein the generating step comprises the step of manufacturing the surgical instrument or prosthesis having a contact surface that is the negative of the modeled surface.

19. A computer implemented method for generating a patient specific model of a body part, comprising the steps of:
processing an x-ray image of a body part of a patient to produce a processed x-ray image, wherein processing the x-ray image includes filtering the x-ray image, generating a differential image corresponding to differences in intensity of the filtered x-ray image and normalizing peaks in the differential image by applying a normalizer function to peaks in the differential image;
reconstructing a CT scan type image using parameters of a model of the body part from a statistical shape model generated using a minimum description length approach and having anatomical correspondences;
generating a pseudo x-ray image corresponding to the x-ray image of the body part from the CT scan type image;
processing the pseudo x-ray image of the body part to generate a processed pseudo x-ray image, wherein processing the pseudo x-ray image includes filtering the pseudo x-ray image, generating a differential image corresponding to differences in intensity of the filtered pseudo x-ray image and normalizing peaks in the differential image by applying a sigmoid function to the differential image; and
using a quasi-optimisation method to minimize a cost function indicating a residual between the processed x-ray image and processed pseudo x-ray image by varying the parameters of the model of the body part to generate a patient specific model of the body part.

* * * * *